United States Patent [19]

Mathew

[11] Patent Number: 5,489,689
[45] Date of Patent: Feb. 6, 1996

[54] PREPARATION OF PIPERIDINE DERIVATIVES

[75] Inventor: Jacob Mathew, Fenton, Mo.

[73] Assignee: Mallinckrodt Chemical, Inc., Chesterfield, Mo.

[21] Appl. No.: 128,993

[22] Filed: Sep. 30, 1993

[51] Int. Cl.$^6$ .................. C07D 211/36; C07D 211/40
[52] U.S. Cl. ............................................. 546/242; 546/243
[58] Field of Search ........................... 546/242, 243

[56] References Cited

U.S. PATENT DOCUMENTS

| | | | |
|---|---|---|---|
| 3,998,834 | 12/1976 | Janssen et al. | 546/223 |
| 4,179,569 | 12/1979 | Janssen et al. | 546/223 |
| 5,106,983 | 4/1992 | Reiff et al. | 546/224 |

FOREIGN PATENT DOCUMENTS 0396282  11/1990  European Pat. Off. .

OTHER PUBLICATIONS

Rosow, Carl E., "Sufentanil Citrate: A New Opiod Analgesic for Use in Anesthesia", *Pharmacotherapy*, vol. 4, No. 1, 1984, pp. 11–19.

Van Daele et al., "Synthetic Analgesics: N–(1–[2–Arylethyl]–4–substituted 4–Piperidinyl) N–Arylalkanamides", *Arzneim.–Forsch.* (Drug Res.), 26, Nr. 8 (1976), pp. 1521–1531.

Niemegeers et al., "Sufentanil, a Very Potent and Extremely Safe Intravenous Morphine–like Compound in Mice, Rats and Dogs", *Arzneim.–Forsch.* (Drug Res.) 26, Nr. 8 (1976) pp. 1551–1556.

Colapret, et al., "Synthesis and Pharmacological Evaluation of 4,4–Disubstituted Piperidines", *J. Med. Chem*, 1989, 32, 968–974.

Brown et al., "An Unusual Reduction of Tertiary Amides with Carbon–Nitrogen Fission", *Communications*, pp. 63–64.

John T. Lai, "Hindered Amines. Synthesis of Hindered Acyclic α–Amino–acetamides", *American Chemical Society*, 1980.

Taber et al. "Amide to Ester Conversion: A Practical Route to the Carfentanil Class of Analgetics," *J. Org. Chem.*, 57:4037–4038 (1992).

*Chemical Abstracts*, vol. 114, No. 25, Abstract No. 247703 (Jun. 24, 1991); and *Nanjing Daxue Xuebao, Ziran Kexue*, 26:4, pp. 667–674 (1990).

Primary Examiner—C. Warren Ivy
Assistant Examiner—Raymond Covington
Attorney, Agent, or Firm—Rothwell, Figg, Ernst & Kurz

[57] ABSTRACT

A piperidine derivative such as sufentanil is formed in a process which includes the step of condensing a piperidone with a primary amine so as to form a 4-amino-4-carboxyamino-piperidine.

37 Claims, 1 Drawing Sheet

PREPARATION OF PIPERIDINE DERIVATIVES

BACKGROUND OF THE INVENTION

1. Field of the Invention

The present invention relates to a process for the preparation of piperidine derivatives including sufentanil citrate.

2. Description of the Background Art

Sufentanil citrate, first synthesized in 1974 (Niemegeers et al., Arzneim. Forsch. 26:1551–1556, 1976), is a piperidine derivative and a member of a series of potent fentanyl analogues. It is a powerful analgesic with an excellent safety margin as compared to other narcotic agents. It is furthermore characterized by a high selectivity and affinity (approximately 10 times greater than fentanyl) for "mu" opiate receptors. Sufentanil produces, unlike fentanyl or morphine, complete anesthesia with minimal side-effects. When compared with fentanyl, its pharmacokinetic profile in man shows a smaller volume of distribution, resulting in a terminal half-life intermediate between alfentanil and fentanyl. Sufentanil in high doses with 100% oxygen in patients undergoing major surgical procedures produces excellent cardiovascular stability and preserves cardiac output and myocardial oxygen balance with minimal changes in heart rate. Furthermore, sufentanil suppresses most hormonal responses to surgical stimulation without producing significant cardiovascular depression. Additionally, sufentanil, like fentanyl, does not cause histamine release. Also, in low to moderate doses, sufentanil may have further advantages over other narcotic agents. When compared with meperidine, morphine and fentanyl, in patients undergoing general surgery under balanced anesthesia, sufentanil provides stable cardiovascular parameters, low preoperative catecholamine plasma levels, very little need for additional inhalation supplementation, and a low incidence of postoperative respiratory depression.

Because of its remarkably low cardiovascular toxicity, sufentanil citrate has been evaluated as a total intravenous anesthetic for major surgical procedures. It is primarily used for open heart surgery and major operations in patients with severe cardiovascular compromise.

The chemical name for sufentanil is N-[ 4-(methoxymethyl)-1[2-(2-thienyl)ethyl]- 4-piperidinyl]-N-phenylpropanamide 2-hydroxy- 1,2,3-propanetricarboxylate. It has an empirical formula of $C_{28}H_{38}N_2O_9S$. Sufentanil citrate is a white crystalline powder (molecular weight=578.68) with a reported melting point of 136.3° C., and is very soluble in water and most common organic solvents.

Synthesis of sufentanil is disclosed in U.S. Pat. No. 3,998,834 to Janssen. The process described therein, however, is quite lengthy and complicated. There remains a need in the art for improved processes for producing piperidine derivatives including sufentanil.

SUMMARY OF THE INVENTION

Figure 1:
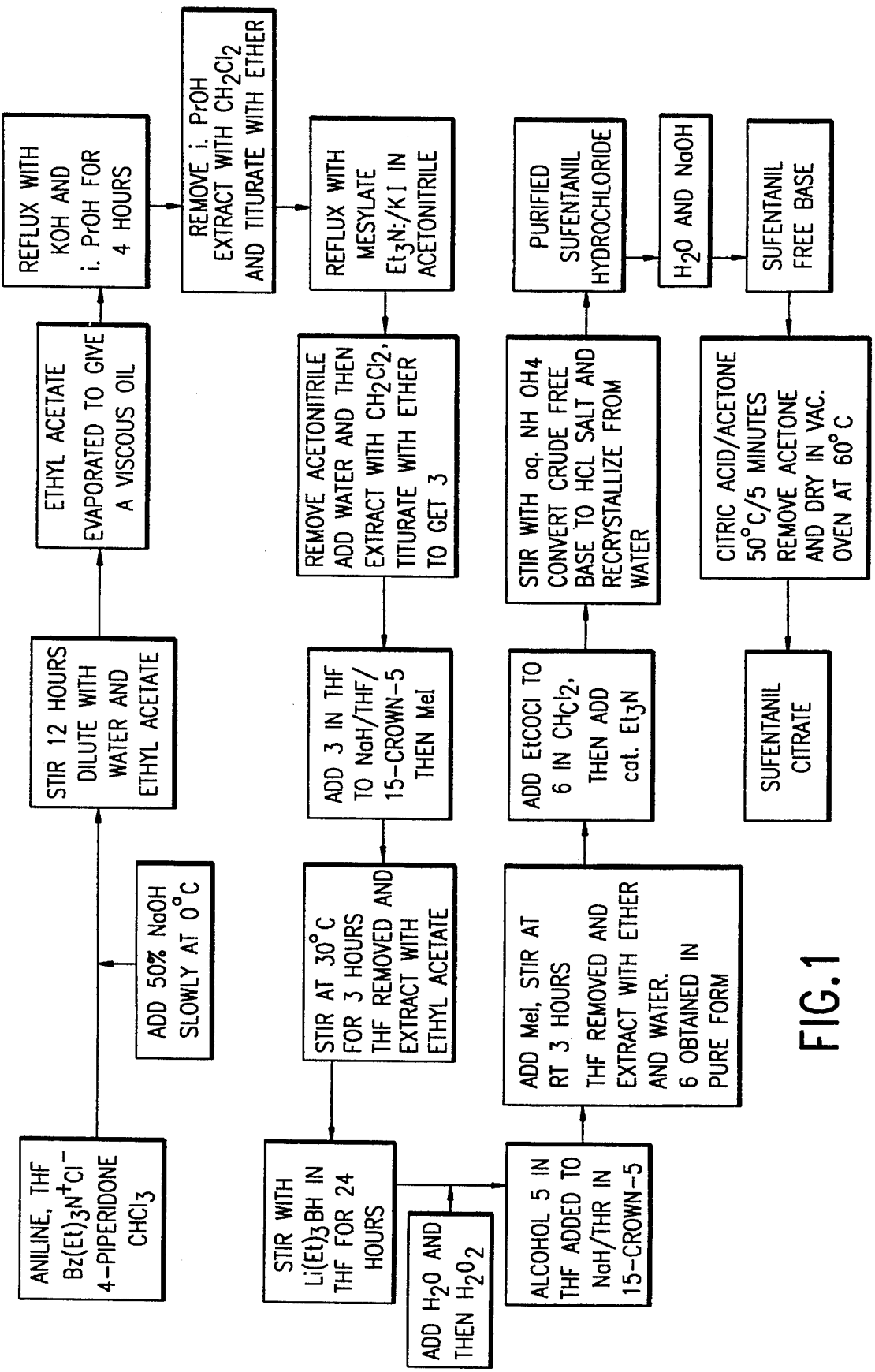
FIG. 1 is a flow sheet for the production of sufentanil citrate utilizing the process of the present invention.

In accordance with the present invention, a process for preparing a piperidine derivative includes the step of condensing a piperidone with a primary amine so as to form a 4-amino-4-carboxyamino-piperidine.

DETAILED DESCRIPTION OF THE PREFERRED EMBODIMENTS

The present invention provides a process for preparing piperidine derivatives.

In accordance with one embodiment of the present invention, a piperidine derivative is prepared by condensing a piperidone with a primary amine, such as aniline, so as to form a 4-amino-4-carboxyamino-piperidine.

In preferred embodiments, the ring nitrogen (N) of both the piperidone and the 4-amino-4-carboxyamino-piperidine includes a —COO—$(CH_2)_n$—$CH_3$ substituent, wherein n is an integer of from zero to about 10.

In particularly preferred embodiments, the piperidone is 1-carbethoxy-4-piperidone, and the 4-amino-4-carboxyamino-piperidine is 1-(carbethoxy)- 4-(phenylamino)-4-piperidine carboxanilide of the formula 1, as shown in the following general scheme.

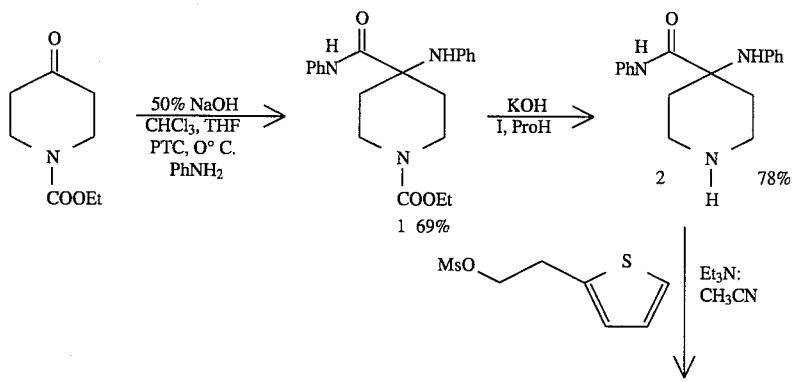

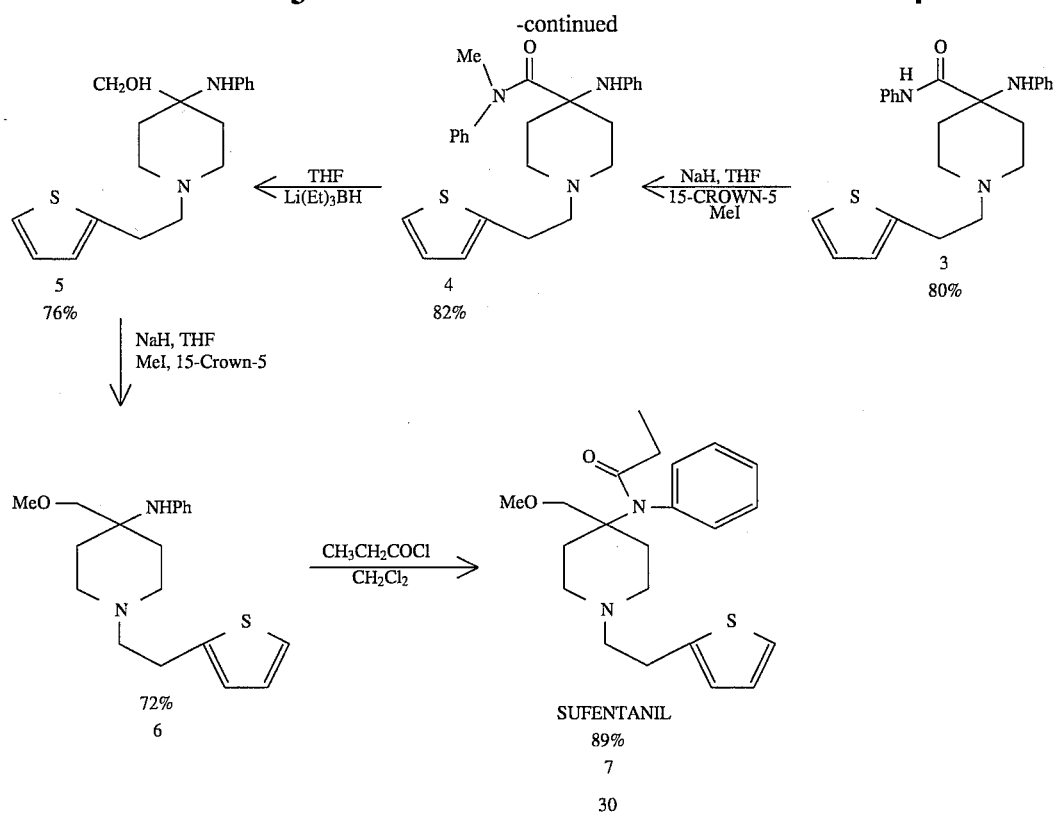

In preferred embodiments, the primary amine with which the piperidone is condensed is aniline. In particularly preferred embodiments, the piperidone is reacted with chloroform to form an intermediate epoxide, which epoxide is then reacted with the primary amine so as to form the 4-amino-4-carboxyamino-piperidine, in accordance with the following scheme.

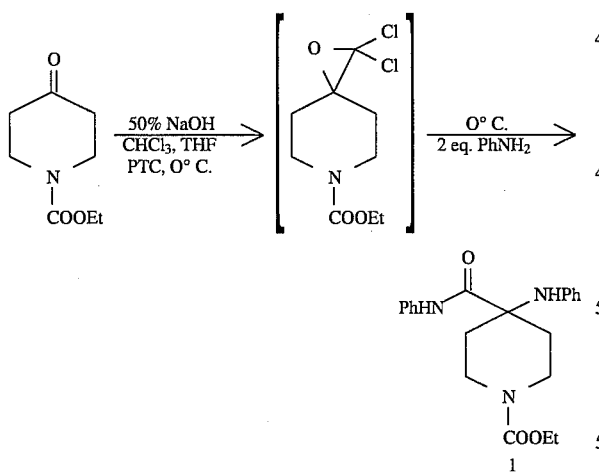

As can be seen in the scheme immediately above, the epoxide formed therein is a dichloroepoxide. In accordance with this embodiment, the epoxide is reacted with the aniline so as to form the compound of formula 1 above.

In accordance with one aspect of the present invention, a 4-amino-4-carboxyamino-piperidine, in which the piperidine ring N includes a —COO—$(CH_2)_n$—$CH_3$ substituent, is hydrolyzed so as to remove the substituent attached to the ring N, and form a piperidine hydrolysis product. This ring N substituent can be hydrolyzed with an excess of alkali base, such as KOH, in an organic solvent such as isopropyl alcohol. In preferred embodiments, the piperidine hydrolysis product thus formed is 4-(phenylamino)-4-piperidinecarboxanilide of formula 2 shown in the general scheme above.

In preferred embodiments, the above piperidine hydrolysis product is condensed with a mesylate (methanesulfonyl) of the formula R—$(CH_2)_m$—O—Ms wherein R is phenyl, thienyl or 4-ethyl-4,5-dihydro-5-oxo- 1H-tetrazol-1-yl, m is an integer of from 1 to about 10, and Ms is methanesulfonyl. The resulting product is an N-substituted R—$(CH_2)_m$-piperidine product, which can be alkylated so as to form a tertiary amide. In the general scheme shown above, the R—$(CH_2)_m$-piperidine product is a piperidinecarboxanilide of the formula 3. A tertiary amide can also be produced by alkylating the 4-amino- 4-carboxyamino-piperidine described above.

In particularly preferred embodiments, the tertiary amide is an anilide of the formula 4 shown in the general scheme above.

In preferred embodiments, a tertiary amide produced as above is reduced so as to form an alcohol. In particular preferred embodiments, the tertiary amide is reduced to the alcohol with a super hydride, such as lithium triethylborohydride, in the presence of an inert organic solvent such as tetrahydrofuran (THF).

The alcohol produced according to the general scheme above is N-(2-thien-2-ylethyl)-4-(phenylamino)- 4-(hydroxymethyl)piperidine of formula 5.

In accordance with one aspect of the invention, the alcohol as formed above is alkylated so as to form an ether having an alkyl portion containing from 1 to about 4 carbon atoms. In preferred embodiments, the alcohol is alkylated with an alkyl halide in the presence of THF and a crown ether, so as to form said ether. In particularly preferred embodiments, the crown ether is 15-crown-5, the alkyl halide is $CH_3I$, and the alkyl portion of the ether contains one carbon atom. In the general scheme above, the ether formed is of the formula 6.

An ether as formed above can be reacted with a compound of the formula $CH_3(CH_2)_xCOCl$, wherein x is an integer of from zero to about 4, so as to form an amide. In preferred embodiments wherein the alkyl portion of the ether has one carbon atom (as in the compound of formula 6), the ether most preferably is reacted with $CH_3CH_2COCl$ so as to form sufentanil, which is formula 7 in the general scheme above. In particularly preferred embodiments, the ether of formula 6 is reacted in methylene chloride so as to form said sufentanil of formula 7.

The sufentanil can be isolated as an HCl salt, converted to a free base, and formed into the citrate salt, as described in the examples below, or by any suitable method.

The invention is further illustrated by the following examples, which are not to be construed as limiting.

Example 1

Preparation of 1-(Carbethoxy)-4-(phenylamino)-4-piperidinecarboxanilide (1)

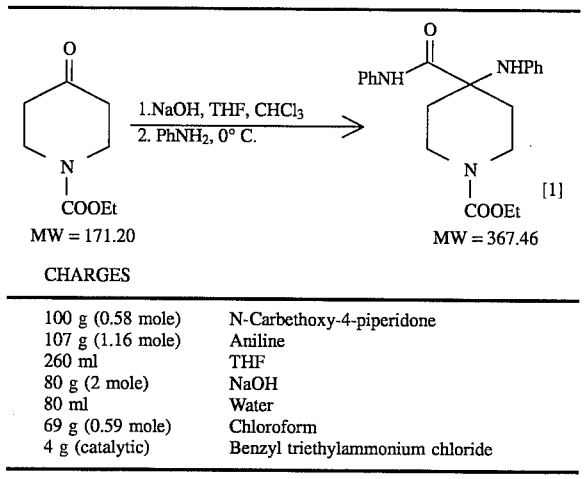

CHARGES

| | |
|---|---|
| 100 g (0.58 mole) | N-Carbethoxy-4-piperidone |
| 107 g (1.16 mole) | Aniline |
| 260 ml | THF |
| 80 g (2 mole) | NaOH |
| 80 ml | Water |
| 69 g (0.59 mole) | Chloroform |
| 4 g (catalytic) | Benzyl triethylammonium chloride |

To a stirred circulating bath cooled solution of piperidone in THF in a 3-necked flask under nitrogen was added chloroform followed by benzyl triethyl ammonium chloride. 1 eq. (0.6 mole, 24 g) of a cold solution of sodium hydroxide in water (25 ml) was added in the course of 15 minutes via a dropping funnel fitted on one neck of the flask so that the inside pot temperature was between 0°–9° C. At the end of addition, aniline was added rapidly. After 5–10 minutes the remaining aqueous sodium hydroxide (56 g in 56 ml water) was added in 5 minutes. After stirring at 5° C. for another 6–7 hours, the mixture was stirred overnight at 10°–12° C., warmed to RT and worked up by stirring with large excess of water (800 ml) and ethyl acetate (2 L) until a clear two phase system resulted. The organic layer was separated, washed with water (100 ml), 2N HCl (2×50 ml) (to remove the aniline), 10% aq. NH4OH (20 ml) and dried. Evaporation of solvent gave yellow viscous mass (150 g) which was about 86% product 1 by GC. Stirring the crude product with a minimum amount of ether (100 ml) gave after filtration pure 1 (97 g, 46% based on piperidone) with the following spectral characteristics.
H$^1$NMR: δ8.95 (s,1H), 7.55–6.65 (m,10H), 4.15 (q,2H), 3.90 (m,2H), 3.10 (t,2H), 2.30 (doft,2H), 1.90 (d,2H), 1.20 (t,3H).
C$^{13}$NMR: δ173.12, 155.49, 143.12, 137.63, 129.50, 129.44, 124.47, 120.34, 119.86, 116.67, 61.49, 59.38, 39.26, 30.95, 14.67. IR(KBR): 3357, 1684, 1498 and 1250 cm$^{-1}$. Mass spectra: 367 (M$^+$), 247, 158.

GC Parameters:
instrument: Variam 3400
column: DB-17 fused silica capillary column 15M×0.53 mm ID, 1 um film thickness
Column Temp initial temperature program 150° C. hold for 2 mins.
program: ramp to 260° C. @10°/minute hold to 260° C. for 5 minutes
injector: Megabore on-column injector @250° C.
detector: FID @300° C. Air 300 mls/min Hydrogen 30 mls/min
Carrier gas: Helium @9.2 mls/min
Makeup gas: Nitrogen @20 mls/min
Sample 1–2 drops of sample dissolved in 5 mls of methanol
preparation: Inject 1 ul of the sample preparation into a prepared gas chromatograph. Electronically integrate the area under each peak excluding methanol solvent front. Results are reported using a standard area technique.

Example 2

Preparation of 4-(Phenylamino)-4-piperidinecarboxanilide (2)

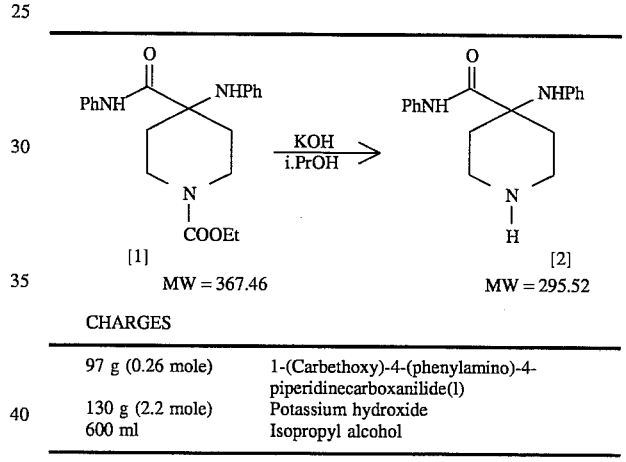

CHARGES

| | |
|---|---|
| 97 g (0.26 mole) | 1-(Carbethoxy)-4-(phenylamino)-4-piperidinecarboxanilide(1) |
| 130 g (2.2 mole) | Potassium hydroxide |
| 600 ml | Isopropyl alcohol |

The charges were refluxed under a slow stream of nitrogen for 3 hours. For the first hour, there was considerable frothing and carbon dioxide evolution. Therefore considerable care was taken to ensure that there was no excess heat applied during this period. After 3 hours of reflux, liquid chromatography (LC) or GC(DB-1) indicated completion of reaction as shown by the disappearance of the starting material peak. Typically, about 96% of 2 was formed at this point as indicated by LC or GC. The dark brown mixture was cooled to room temperature (RT) and most of isopropyl alcohol evaporated at around 65° C. The residue diluted with water (300 ml) and methylene chloride (500 ml) and stirred for 5 minutes. The organic layer was separated and washed with water (2×40 ml), dried over anhydrous magnesium sulfate and solvents evaported to give brown viscous mass. This was stirred with ether (100 ml) at room temperature (RT) for 15 minutes. The thick yellow cake was filtered off, washed with a small amount of cold ether, and air-dried to get 2 (66 g) as a pale yellow powder. LC showed 99% purity. Isolated yield= 86%. H$^1$NMR: δ9.05 (s,1H), 7.60–6.65 (m,10H), 4.10 (s,2H), 3.05 (d,2H), 2.80 (t,2H), 2.30 (t,2H), 1.90 (d,2H), 1.70 (s,1H).
C$^{13}$NMR: δ173.73, 143.35, 137.70, 129.29, 128.89, 124.14, 119.9, 116.64, 59.77, 41.61, 31.97. IR(KBR): 3325, 1674, 1496, 1441 cm$^{-1}$. Mass spectra: 295 (M$^+$), 175, 145.

GC Parameters:
instrument: Varian 3400
column: DB-1 fused silica capillary column 15M×0.53 mm ID, 1 um film thickness
Column Temp initial temperature program 230° C. hold for 2 mins.
program: ramp to 310° C. @10°/minute hold to 310° C. for 5 minutes
injector: Megabore on-column injector @250° C.
detector: FID @300° C. Air 300 mls/min Hydrogen 30 mls/min
Carrier gas: Helium @9.2 mls/min
Makeup gas: Nitrogen @20 mls/min
Sample 1–2 drops of sample dissolved in 5 mls of methanol
preparation: Inject 1 ul of the sample preparation into a prepared gas chromatograph. Electronically integrate the area under each peak excluding methanol solvent front. Results are reported using a standard area technique.

Example 3

Preparation of 2-(2-thienyl)ethanol methanesulfonate

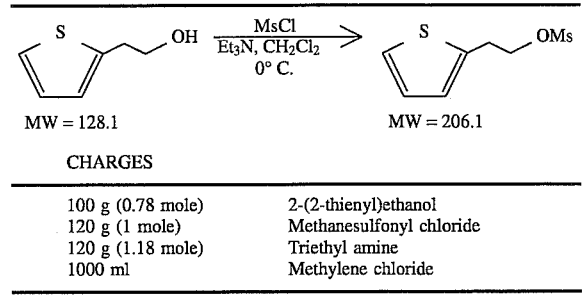

CHARGES

| 100 g (0.78 mole) | 2-(2-thienyl)ethanol |
| 120 g (1 mole) | Methanesulfonyl chloride |
| 120 g (1.18 mole) | Triethyl amine |
| 1000 ml | Methylene chloride |

The alcohol in methylene chloride was stirred with triethylamine (1.5 eq) at ice bath temperature. Then methanesulfonyl chloride (1.3 eq) was added dropwise to control the exotherm. After 6 hours at RT the mixture washed with water (2×200 ml), aq. sodium bicarbonate (2×100 ml), dried over anhydrous magnesium sulfate and solvent evaporated to give the crude mesylate (144 g, 92%) as a yellow range oil. GC analysis showed 97% purity. This mesylate was used immediately for the next example and is stable for extended periods if stored in the refrigerator. NMR(CDCl$_3$): δ7.20 (1H,m), 6.95 (2H,m), 4.45 (2H,t), 3.27 (2H,t) and 2.91 (3H,s).

GC Parameters:
instrument: Varian 3400
column: DB-17 fused silica capillary column 15M×0.53 mm ID, 1 um film thickness
Column Temp initial temperature program 150° C. hold for 2 mins.
program: ramp to 260° C. @10°/minute hold to 260° C. for 5 minutes
injector: Megabore on-column injector @200° C.
detector: FID @300° C. Air 300 mls/min Hydrogen 30 mls/min
Carrier gas: Helium @9.2 mls/min
Makeup gas: Nitrogen @20 mls/min
Sample 1–2 drops of sample dissolved in 5 mls of methanol
preparation: Inject 1 ul of the sample preparation into a prepared gas chromatograph. Electronically integrate the area under each peak excluding solvent front. Results are reported using a standard area percent technique.

Example 4

Preparation of N-(2-Thien-2-ylethyl)-4-piperidinecarboxanilide (3)

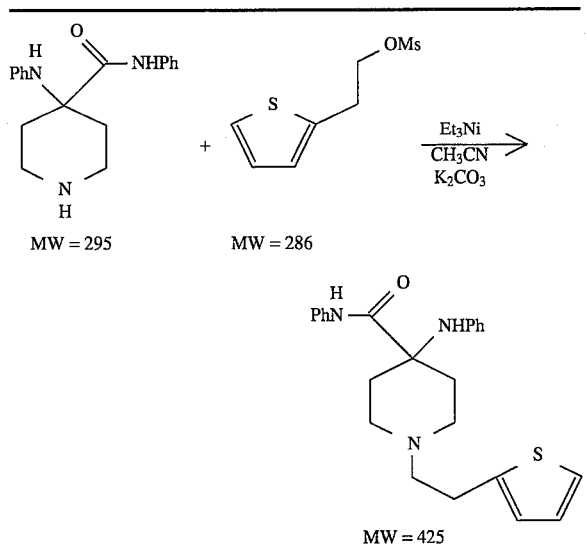

CHARGES

| 42 g (0.145 mole) | 4-(Phenylamino)-4-piperidinecarboxanilide (2) |
| 35 g (0.175 mole) | 2-(2-thienyl)ethanol methanesulfonate |
| 2 g (catalytic) | Potassium carbonate |
| 0.5 g (catlytic) | Potassium iodide (KI) |
| 400 ml | Acetonitrile |
| 30 G (0.29 mole) | Triethyl amine |

The piperidine and the mesylate were dissolved in acetonitrile in a 1-liter flask. Then anhydrous potassium carbontare was added in one portion followed by KI and triethyl amine. The mixture stirred under nitrogen, gently refluxed and analysed by GC every hour. At the end of 4 hours, the maximum yield of 3 was noted with only traces of starting material left. The reaction mixture was cooled to RT and most of the acetonitrile evaporated under vacuum. Water (200 ml) and methylene chloride (400 ml) were added, stirred for 5 minutes, the organic layer separated, washed with water (2×30 ml), dried and solvent removed to obtain yellow brown solid mass. Trituration with ether (100 ml) gave 3 (46 g) as a yellow powder with a GC purity of 98% and LC purity of 95% with no trace of 2 detected. The isolated yield was 80%.

H$^1$NMR: δ9.05 (s,1H), 7.8–6.65 (m, 13H), 4.10 (s,1H), 3.05–1.90 (m,12H). C$^{13}$NMR: δ172.27, 142.36, 141.54, 136.67, 128.44, 127.94, 125.54, 123.53,123.55, 122.92, 118.86, 115.56, 68.73, 58.76, 47.81, 36.40, 30.24, 26.72. Mass spectra: 406 (M+1), 308. IR(KBR): 3407, 3343, 1665, 1602, 1533, 1442 cm$^{-1}$.

GC Parameters:
instrument: Varian 3400
column: DB-1 fused silica capillary column 15M×0.53 mm ID, 1 um fil thickness
Column Temp inital temperature program 230° C. hold for 2 mins.
program: ramp to 310° C. @10°/minute hold to 310° C. for 5 minutes
injector: Megabore on-column injector @250° C.
detector: FID @300° C. Air 300 mls/min Hydrogen 30 mls/min Carrier gas: Helium @9.2 mls/min
Makeup gas: Nitrogen @20 mls/min
Sample 1–2 drops of sample dissolved in 5 mls of methanol preparation: Inject 1 ul of the sample preparation into a prepared gas chromatograph. Electronically integrate the area under each peak excluding methanol solvent front. Results are reported using a standard area technique.

Example 5

Preparation of N-(2-Thien-2-ylethyl)-4-(phenylamino)-4-piperidinecarbox (N-methyl) anilide (4)

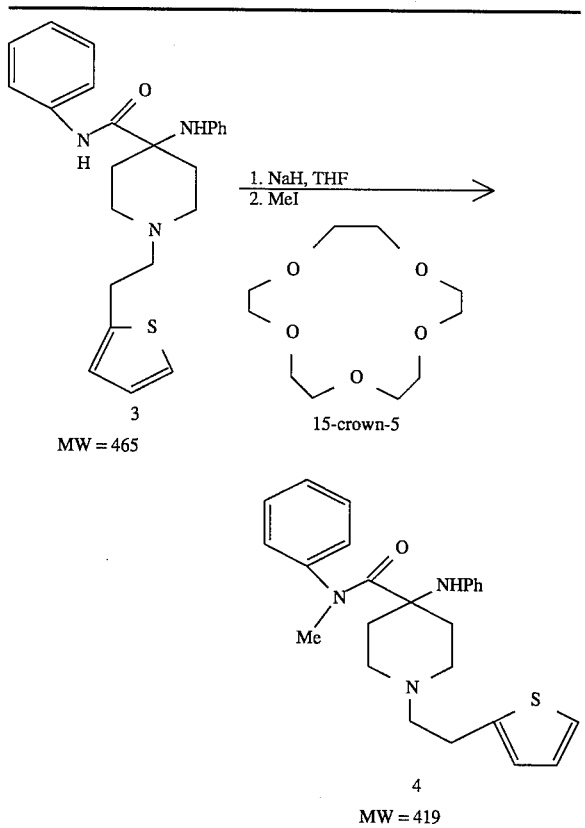

CHARGES

| | |
|---|---|
| 45 g (0.107 mole) | N-(2-Thien-2-ylethyl)-4-(phenylamino)-4-piperidinecarboxanilide(3) |
| 3.45 g (0.135 mole) | Sodium hydride (95%) |
| 48 ml (0.15 mole) | 15-crown-5 |
| 250 ml | THF |
| 17.8 g (0.12 mole) | Methyl Iodide |

Amide 3 was dissolved in THF and added slowly via dropping funnel to a stirred suspension of 95% sodium hydride powder in THF/15-crown-5 contained in a 3-neck-1-liter flask at ambient temperature under nitrogen blanket. When the initial exotherm and frothing was over (30 minutes), the tan suspension was warmed to 50° C. for 45 min using a constant temperature heating controller. At this point a clear greenish tan solution resulted. The reaction mixture was then cooled to RT and methyl iodide was added slowly via the dropping funnel at such a rate that the inside pot temperature did not rise above 40° C. A thick white precipitate formed on completion of addition and after 2 hours at ambient temperature, GC analysis showed no trace of 3.

Most of the THF was removed using a rotary evaporator and the residue diluted with water (200 ml) and ethyl acetate (600 ml). The organic layer separated, washed with water (3×30 ml), dried over anhydrous potassium carbonate (20 g) and solvents evaported to give crude brown powder which was stirred with t-butyl methyl ether (50 ml) for 5 minutes and filtered to obtain 4 (37 g) as pale yellow powder. The isolated yield of 4 was 82% with an LC purity of 95%, while GC showed 99% purity. $H^1$NMR: δ 7.40–6.45 (m,13H), 3.20 (s,3H), 2.90–2.10 (m,12H), 1.65 (s,1H). $C^{13}$NMR: δ174.49, 144.41, 142.89, 129.15, 128.71, 127.53, 127.35, 126.53, 124,56, 123.50, 117.55, 114.37, 70.51, 59.80, 58.90, 48.74, 32.92, 27.83. IR(KBR): 3375, 1628, 1602, 1592, 1492, 1367, 749, 712 $cm^{-1}$. Mass spectra: 419 ($M^+$), 322, 285, 189.

GC Parameters:
instrument: Varian 3400
column: DB-1 fused silica capillary column 15M×0.53 mm ID, 1 um film thickness
Column Temp initial temperature program 230° C. hold for 2 mins.
program: ramp to 310° C. @10°/minute hold to 310° C. for 5 minutes
injector: Megabore on-column injector @250° C.
detector: FID @300° C. Air 300 mls/min Hydrogen 30 mls/min
Carrier gas: Helium @9.2 mls/min
Makeup gas: Nitrogen @20 mls/min
Sample 1–2 drops of sample dissolved in 5 mls of methanol preparation: Inject 1 ul of the sample preparation into a prepared gas chromatograph. Electronically integrate the area under each peak excluding methanol solvent front. Results are reported using a standard area technique.

Example 6

Preparation of N-(2-Thien-2-ylethyl)-4-(phenylamino)-4-(hydroxymethyl) piperidine (5)

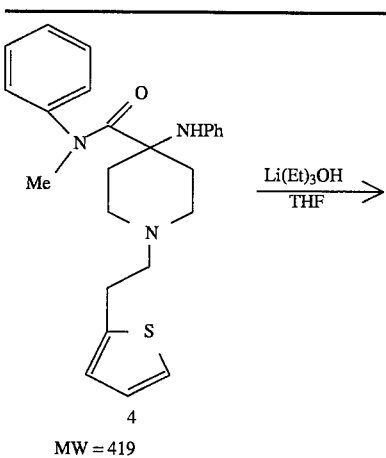

-continued

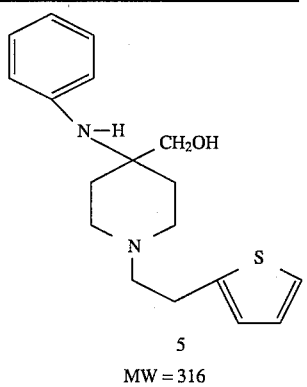

5
MW = 316

CHARGES

| 37 g (0.09 mole) | N-(2-Thien-2-ylethyl)-4-(phenylamino)-4-piperidinecarbox(N-methyl)anilide (4) |
| --- | --- |
| 360 ml (0.36 mole) | 1M Lithium triethylborohydride (Li(Et)₃BH) in THF |
| 60 ml | Tetrahydrofuran(THF) |
| 30 ml | Water |
| 140 ml | 30% H₂O₂ |

A solution of 4 in THF was added rapidly to stirred 1M solution of Lithium triethylborohydride in THF at RT under a nitrogen blanket. The reaction was followed by LC and appeared to be complete after 24 hours at RT. An aliquot (1 ml) was quenched first with water and then with 30% H$_2$O$_2$. LC analysis showed the presence of 85% product and less than 2% starting material along with N-methyl aniline (RT=2.25) and amine 9 (<5%). The reaction mixture was cooled with ice and the calculated amount of water (4 molar equivalents) was first added dropwise to decompose the excess hydrides and complexes. After 10 minutes, 30% hydrogen peroxide (3 equivalents for every mole of alkyl borane) was added dropwise to oxidise the triethyl borane amine complexes. The oxidation was very exothermic and efficient cooling was necessary. The dropwise addition required about 30–40 minutes. The thick slurry that formed was filtered and the salts washed with THF. Most of the THF was removed under vacuum at 50°–55° C. and the residue stirred with methylene chloride (500 ml) and water (200 ml). The organic layer dried and evaporated to give yellow mass. Titration with butyl ether removed N-methylaniline. Alcohol 5 (22 g) obtained as pale yellow powder had a GC purity of 100%, LC purity of 97% and Proton NMR integrated perfectly. The isolated yield of 5 was 78%. H¹NMR (CDCl₃): δ7.40–6.80 (m,8H), 3.75 (s,2H), 3.40 (s,1H), 3.05 (t,2H), 2.75 (t,4H), 2.45 (t,2H), 2.05 (d,2H), 1.79 (t,2H). C13NMR: δ1.45.14, 142.80, 129.24, 126.61, 124.60, 123.51, 120.04, 118.60, 67.44, 60.04, 5573, 49.16, 32.76, 27.92. IR(KBR): 3379, 3112, 1604, 1442, 1306 849, 694 cm⁻¹.
Mass spectra: 317 (M+ 1)⁺, 219.
GC Parameters:
instrument: Varian 3400
column: DB-1 fused silica capillary column 15M×0.53 mm ID, 1 um film thickness
Column Temp initial temperature program 230° C. hold for 2 mins.
program: ramp to 310° C. @10°/minute hold to 310° C. for 5 minutes
injector: Megabore on-column injector @250° C.
detector: FID @300° C. Air 300 mls/min Hydrogen 30 mls/min
Carrier gas: Helium @9.2 mls/min Makeup gas: Nitrogen @20 mls/min
Sample 1–2 drops of sample dissolved in 5 mls of methanol
preparation: Inject 1 ul of the sample preparation into a prepared gas chromatograph. Electronically integrate the area under each peak excluding methanol solvent front. Results are reported using a standard area technique.

Example 7

Preparation of N-(2-Thien-2-ylethyl)-4-(phenylamino)-4-(methoxymethyl)piperidine (6)

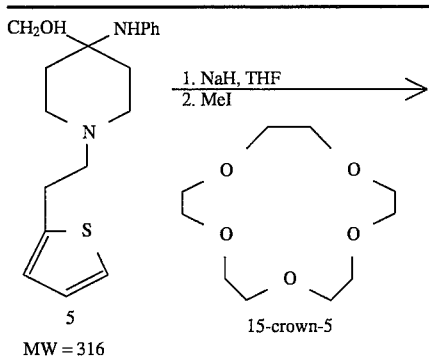

5
MW = 316

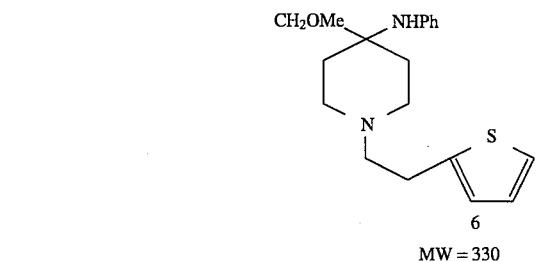

6
MW = 330

CHARGES

| 22 g (0.07 mole) | N-(2-Thien-2-ylethyl)-4-(phenylamino)-4-(hydroxymethyl)piperidine (5) |
| --- | --- |
| 2.06 g (0.083 mole) | NaH |
| 12 G (0.085 mol) | Methyl Iodide |
| 140 ml | THF |
| 28 ml (0.1 mol) | 15-crown-5 |

The alcohol was dissolved in THF and added slowly via dropping funnel to a stirred suspension of 95% sodium hydride powder in THF/15-crown-5 contained in a 3-neck-1-liter flask at ambient temperature under nitrogen blanket. When the initial exotherm and frothing was over (30 minutes), the tan suspension was warmed to 45° C. for about 50 min using a constant temperature heating controller. At that point a clear greenish tan solution results. After cooling to ambient temperature, methyl iodide was then added slowly via the dropping funnel at such a rate that the inside pot temperature did not rise above 40° C. A thick white precipitate formed and after 2 hours at ambient temperature, LC analysis showed less than 3% of alcohol. Most of the THF was removed under vacuum and the residue diluted with water (100 ml) and t-butyl methyl ether (500 ml). The organic layer was washed with water (3× 30 ml), dried over anhydrous potassium carbonate (10 g) and solvents evaporated to give crude ether 6 which had an LC purity of 87%. The traces of alcohol 5 (3%) were easily removed from 6 by dissolving in the minimum amount of ethyl ether and filtering through silica gel (about 3 gm of silica gel for every gm of compound) applied on a fritted funnel using ether as the eluting solvent. The filtrate as shown by LC was at least 99% pure 6. The highly polar alcohol 5 is retained by the silica gel. The isolated yield of 6 (18 g) obtained as pale yellow powder was 78%. H¹NMR (CDCl₃): δ7.35– 6.80 (m,8HO, 3.35 (s,2HO, 3.30 (s,3H), 3.05 (t,2HO, 2.65 (m,6H), 2.05–1.7 (m,4H). C¹³NMR: δ 145.14, 142.80, 129.24, 126.61, 124.60, 123.51, 120.04, 118.60, 67.44, 63.45, 60.04, 55.73, 49.16, 32.76, 27.92. IR(KBR): δ3354, 2812, 1601, 1111, 1253, 851, 700 cm⁻¹. Mass Spectra: 330 (M⁺), 285, 233.

HPLC CONDITIONS

| Column: | Hypersil ODS (C18) 4.6 mm × 25 cm 5 um |
|---|---|
| Temperature: | Ambient |
| Flow rate: | 2 mls/minute |
| Detection: | 0.1 auf @ 220 nm |
| Injection: | 25 ul |

Mobile Phase: 450:310:240 Methanol: ammonium acetate soln. (1/100): Acetonitrile. Adjust pH to 7.2 by the addition of glacial acetic acid. Filter and degas. Isocratic 15 min run.
Blank—prepared a blank containing 16.5 mg of citric acid in 100 ml of mobile phase. Inject this blank along with samples.
Sample preparation—weigh 8–10 mg of sufentanil citrate in 10 ml volumetric flask, dilute to volume with mobile phase. Dilute 1 ml into a 10 ml volumetric and dilute to volume with mobile phase. Integrate all peaks in the samples chromatograms disregarding any peaks in the blank preparation. Results are determined by area percent calculation.

Example 8

Preparation of N-[4-(Methoxymethyl)-1-{2-(2-thienyl)ethyl}-4-piperidinyl]-N-phenylpropanamide (7)

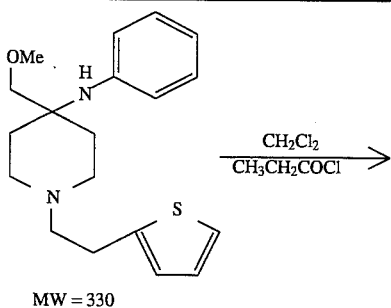

MW = 330

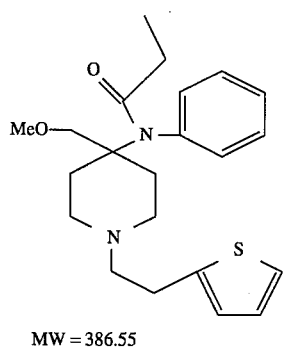

MW = 386.55

CHARGES

| 18 g (0.055 mole) | N-(2-Thien-2-ylethyl)-4-(phenylamino)-4- |
|---|---|
| 6.7 g (0.07 mole) | (methoxymethyl)piperidine (6) |
| | Propionyl chloride |
| 150 ml | Methylene chloride |

Propionyl chloride (1.3 equivalents) was added to a 0.4M methylene chloride solution of 6 in a glass stoppered RB flask at RT. A mild exotherm developed and analysis by LC at the end of 40 minutes showed 90% sufentanil 7 with about 7% starting material 6. About 8% by weight of triethylamine was then added and stirred for another 40 minutes at RT. LC showed 95% product with no trace of starting material 6. The mixture was then quenched with an excess of dilute ammonium hydroxide and the lower methylene chloride layer was separated, washed with water and dried. Evaporation of methylene chloride gave a yellow powder which by LC amounted to 95% sufentanil 7. This was converted to HCl salt by dissolving in ether (250 ml) and stirring with 4N HCl [ 100 ml]. The precipitated HCl salt was filtered off, washed with ether and air-dried. Recrystallization from water (6 ml for every gm of Sufentanil.HCl) gave sufentanil HCl (19.6 g) as white paste with LC purity of 99.50%. The isolated yield of the pure HCl salt was 85%. H¹NMR (CDCl₃): δ 7.25–6.85 (m,8H), 4.05 (s,2H), 3.35 (s,3H), 3.14–1.56 (m,14H), 0.95 (t,3H).
C¹³NMR: δ

HPLC CONDITIONS

| Column: | Hypersil ODS (C18) 4.6 mm × 25 cm 5 um |
|---|---|
| Temperature: | Ambient |
| Flow rate: | 2 mls/minute |
| Detection: | 0.1 auf @ 220 nm |
| Injection: | 25 ul |

Mobile Phase: 450:310:240 Methanol:ammonium acetate soln. (1/100): Acetonitrile. Adjust pH to 7.2 by the addition of glacial acetic acid. Filter and degas.
Isocratic 15 min run.
Blank—prepare a blank containing 16.5 mg of citric acid in 100 ml of mobile phase. Inject this blank along with samples.
Sample preparation—weigh 8–10 mg of sufentanil citrate in 10 ml volumetric flask, dilute to volume with mobile phase. Dilute 1 ml into a 10 ml volumetric and dilute to volume with mobile phase. Integrate all peaks in the samples chromatograms disregarding any peaks in the blank preparation. Results are determined by area percent calculations.

Example 9

Sufentanil HCl obtained in Example 8 was suspended in hot water and adjusted to pH 10–11 with 10% aqueous potassium hydroxide and extracted with ether. The organic layer washed with water, dried and evaporated to give the free base with an LC purity profile of 99.62%. An equivalent of sufentanil free base with anhydrous citric acid was warmed in 100% ethanol. After removal of ethanol the fluffy white powder was dried in the vacuum oven at 56° C. for 48 hrs. Sufentanil citrate thus obtained passed all USP tests.

The present invention provides a new process for preparing piperidine derivatives, including a new efficient eight step synthesis of sufentanil citrate starting from the readily available 1-carbethoxy-4-piperidone. This synthesis eliminates an initial potassium cyanide step of a previous 12 step process and is of major significance from a safety and environmental point of view. This process eliminates the use of several reagents used in the previous process, and provides for easy isolation and identification of all the intermediates. Overall production time and cost have been significantly reduced. The new process is sufficiently versatile enough to be applied for the synthesis of alfentanil and analogs and is superior to previous synthesis of this class of compounds all of which use potassium cyanide in an initial step.

Since many modifications, variations and changes in detail may be made to the described embodiments, it is intended that all matter in the foregoing description and shown in the accompanying drawing be interpreted as illustrative and not in a limiting sense.

What is claimed is:

1. A process for preparing a piperidine derivative which comprises, condensing a piperidone with a primary amine so as to form a 4-amino- 4-carboxyamino-piperidine, wherein N of said piperidone and N of the piperidine portion of said 4-amino-4-carboxyamino-piperidine is a —N—COO—$(CH_2)_n CH_3$, wherein n is an integer of from 0 to about 10, further including the step of hydrolyzing said —COO—$(CH_2)_n CH_3$ group of said 4-amino-4-carboxyamino-piperidine following the condensation reaction so as to form a piperidine hydrolysis product, wherein said piperidine hydrolysis product is condensed with a mesylate (methanesulfonyl) of the formula R—$(CH_2)_m$—O—Ms, wherein R is phenyl, thienyl or 4-ethyl-4,5-dihydro- 5-oxo-1H-tetrazol-1-yl, m is an integer of from 1 to about 10 and Ms is methanesulfonyl, so as to form an N-substituted R—$(CH_2)_m$-piperidine product.

2. The process of claim 1 wherein, said primary amine is aniline.

3. The process of claim 1 wherein, during formation of said 4-amino-4-carboxyamino-piperidine, said piperidone is reacted with chloroform to form an intermediate epoxide, which epoxide is then reacted with said primary amine to form said 4-amino-4-carboxyamino-piperidine.

4. The process of claim 3 wherein said epoxide is a dichloroepoxide.

5. The process of claim 1 wherein, the piperidone is 1-carbethoxy-4-piperidone.

6. The process of claim 5 wherein the 4-amino- 4-carboxyamino-piperidine is 1-(carbethoxy)- 4-(phenylamino)-4-piperidinecarboxanilide.

7. The process of claim 1 wherein the piperidine hydrolysis product is 4-(phenylamino)-4-piperidinecarboxanilide.

8. The process of claim 1 wherein said —COO—$(CH_2)_n CH_3$ group is hydrolyzed with an excess of an alkali base in an organic solvent.

9. The process of claim 8 wherein said alkali base is KOH and said organic solvent is isopropyl alcohol.

10. A process for preparing a piperidine derivative which comprises condensing a 4-amino- 4-carboxyamino-piperidine with a mesylate (methanesulfonyl) R—$(CH_2)_m$—O—Ms, wherein R is phenyl, thienyl or 4-ethyl-4,5-dihydro-5-oxo-1 H-tetrazol-1-yl, m is an integer of from 1 to about 10 and Ms is methanesulfonyl, so as to form an N-substituted R—$(CH_2)_m$-piperidine product.

11. The process of claim 10 further comprising the step of alkylating said R—$(CH_2)_m$-piperidine product so as to form a tertiary amide.

12. The process of claim 11 further including the step of reducing said tertiary amide so as to form an alcohol.

13. The process of claim 12 wherein said tertiary amide is reduced to said alcohol with a super hydride.

14. The process of claim 13 wherein said super hydride is lithium triethylborohydride.

15. The process of claim 12 wherein, said alcohol is N-(2-thien-2-ylethyl)-4-(phenylamino)- 4-(hydroxymethyl)piperidine.

16. The process of claim 12 wherein the reducing step is carried out in an inert organic solvent.

17. The process of claim 16 wherein said inert organic solvent is THF.

18. The process of claim 12 further including the step of alkylating said alcohol so as to form an ether having an alkyl portion containing from 1 to about 4 carbon atoms.

19. The process of claim 18 wherein said alcohol is alkylated with an alkyl halide in the presence of THF and a crown ether.

20. The process of claim 19 wherein the crown ether is 15-crown-5.

21. The process of claim 20 wherein the alkyl halide is CH$_3$I, and said alkyl portion contains one carbon atom.

22. The process of claim 20 further including step of reacting said ether with $CH_3(CH_2)_x COCl$, wherein x is an integer of from 0 to about 4, so as to form an amide.

23. The process of claim 22 wherein the alkyl portion of said ether has one carbon atom, and said ether is reacted with $CH_3CH_2COCl$ so as to form sufentanil.

24. The process of claim 23 wherein said ether is reacted in methylene chloride to form said sufentanil.

25. The process of claim 23, further including the step of converting said sufentanil to the citrate salt of sufentanil.

26. A process for preparing a piperidine derivative which comprises, a) condensing 1-carbethoxy-4-piperidone with a primary amine so as to form 1-(carbethoxy)-4-(phenylamino)-4-piperidinecarboxanilide;

b) hydrolyzing said 1-(carbethoxy)-4-(phenylamino)-4-piperidinecarboxanilide as to form 4-(phenylamino)-4-piperidinecarboxanilide;

c) condensing said 4-(phenylamino)- 4-piperidinecarboxanilide with a mesylate (methanesulfonyl) of the formula R—$(CH_2)_m$—O—Ms wherein R is phenyl, thienyl or 4-ethyl-4,5-dihydro-5-oxo-1 H-tetrazol-1-yl, m is an integer of from 1 to about 10 and Ms is methanesulfonyl, so as to form an N-substituted R—$(CH_2)_m$-piperidine product;

d) alkylating said R—$(CH_2)_m$-piperidine product so as to form a tertiary amide;

e) reducing said tertiary amide so as to form an alcohol, wherein said alcohol is N-(2-thien-2-ylethyl)- 4-(phenylamino)-4-(hydroxymethyl)piperidine;

f) alkylating said alcohol so as to form an ether;

g) reacting said ether with $CH_3CH_2COCl$ so as to form sufentanil; and h) converting said sufentanil to a citrate salt of sufentanil.

27. A process for preparing a piperidine derivative which comprises, condensing a piperidone with a primary amine so as to form a 4-amino- 4-carboxyamino-piperidine, wherein N of said piperidone and N of the piperidine portion of said 4-amino- 4-carboxyamino-piperidine includes a —COO—$(CH_2)_n CH_3$ substituent, wherein n is an integer of from 0 to about 10, wherein said condensing takes place in the presence of THF.

28. The process of claim 11, wherein said tertiary amide is formed in the presence of a crown ether.

29. The process of claim 28, wherein said crown ether is 15-crown-5.

30. A compound of the formula

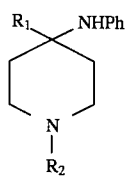

wherein $R_1$ is —CONHPh and $R_2$ is H, $R_1$ is —CONHPh and $R_2$ is R—$(CH_2)_m$—, $R_1$ is —CONCH$_3$Ph and $R_2$ is R—$(CH_2)_m$—, $R_1$ is —CH$_2$OH and $R_2$ is R—$(CH_2)_m$—, or $R_1$ is —CH$_2$OCH$_3$ and $R_2$ is R—$(CH_2)_m$—; and wherein Ph is phenyl, R is Ph, thienyl or 4-ethyl-4,5-dihydro- 5-oxo-1H-tetrazol-1-yl and n is an integer of from 1 to about 10.

31. The compound of claim 30, wherein $R_1$ is —CONHPh and $R_2$ is H.

32. The compound of claim 30, wherein R is thienyl.

33. The compound of claim 32, wherein m is 2.

34. The compound of claim 33, wherein $R_1$ is —CONHPh.

35. The compound of claim 33, wherein $R_1$ is —CONCH$_3$Ph.

36. The compound of claim 33, wherein $R_1$ is —CH$_2$OH.

37. The compound of claim 33, wherein $R_1$ is —CH$_2$OCH$_3$.

* * * * *

UNITED STATES PATENT AND TRADEMARK OFFICE
CERTIFICATE OF CORRECTION

PATENT NO. : 5,489,689

DATED : February 6, 1996

INVENTOR(S) : Jacob Mathew

It is certified that error appears in the above-indentified patent and that said Letters Patent is hereby corrected as shown below:

Col. 5, line 56, "NH4OH" should be -- $NH_4OH$ --; Col. 8, line 32, in the table, the fourth entry under the subheading "CHARGES", "catlytic" should be -- catalytic --; Col. 11, line 51, delete "C"; Col. 11, line 52, "$_{13}$NMR" should be -- $C_{13}$NMR --; Col. 11, line 52, "1.45.14" should be -- 145.14 --; Col. 11, line 53, "5573" should be -- 55.73 --; Col. 11, line 54, after "1306" insert a comma; Col. 13, line 5, "(m,8HO" should be -- (m,8HO) --; same line, "(s,2HO" should be -- (s,2HO) --; same line, "(t,2HO" should be -- (t,2HO) --; Col. 13, line 8, delete "$\delta$"; Col. 13, line 9, "1111, 1253" should be -- 1253, 1111 --;

In the Claims: Col. 16, line 17 (claim 21), delete "CH"; Col. 16, line 18 (claim 21), delete "$_3$I" should be -- $CH_3I$ --.

Signed and Sealed this

Twenty-fifth Day of June, 1996

Attest:

BRUCE LEHMAN

Attesting Officer

Commissioner of Patents and Trademarks